(12) United States Patent
Cobler et al.

(10) Patent No.: US 10,240,979 B2
(45) Date of Patent: Mar. 26, 2019

(54) PULSE GENERATOR AND SYSTEMS AND METHODS FOR USING SAME

(71) Applicant: Cascodium Inc., Andover, MA (US)

(72) Inventors: Patrick J. Cobler, Nashua, NH (US); Scott A. Rhodes, North Andover, MA (US); Paul D. Butler, Methuen, MA (US); Neal R. Butler, Acton, MA (US); Michael R. Dynok, Byfield, MA (US)

(73) Assignee: Cascodium Inc., Andover, MA (US)

( * ) Notice: Subject to any disclaimer, the term of this patent is extended or adjusted under 35 U.S.C. 154(b) by 734 days.

(21) Appl. No.: 14/753,775

(22) Filed: Jun. 29, 2015

(65) Prior Publication Data
US 2015/0300878 A1   Oct. 22, 2015

Related U.S. Application Data
(62) Division of application No. 13/181,745, filed on Jul. 13, 2011, now Pat. No. 9,072,169.
(Continued)

(51) Int. Cl.
  *G01J 3/10* (2006.01)
  *H05K 9/00* (2006.01)
  (Continued)

(52) U.S. Cl.
  CPC ............ *G01J 3/10* (2013.01); *G01J 3/0291* (2013.01); *G01J 3/443* (2013.01); *H05H 1/46* (2013.01);
  (Continued)

(58) Field of Classification Search
  CPC .... G01N 21/67; G01J 3/443; H01J 37/32055; G02B 6/2551
  See application file for complete search history.

(56) References Cited

U.S. PATENT DOCUMENTS

| 1,971,215 A | 8/1934 | Feussner |
| 2,414,363 A | 1/1947 | Dietert et al. |
| (Continued) | | |

FOREIGN PATENT DOCUMENTS

| WO | 9915865 | 4/1999 |

OTHER PUBLICATIONS

Walters, J.P., "Historical Advances In spark Emission Spectroscopy", Applied Spectroscopy, 1969, pp. 317-331, vol. 23, No. 4.
(Continued)

*Primary Examiner* — Maurice Smith
(74) *Attorney, Agent, or Firm* — Grossman, Tucker, Perreault & Pfleger, PLLC

(57) ABSTRACT

A pulse generator generates high voltage discharge pulses in a manner that may be controlled and monitored. Pulse generator operation may be monitored to measure characteristics associated with pulse generator operation and to produce pulse generator data representative of those characteristics. Pulse generator operation may be monitored by monitoring the discharge pulses produced by the pulse generator and/or the charging of energy storage elements within the pulse generator in preparation for a subsequent discharge pulse. The pulse generator data may be used, for example, to identify pulse generator wear or degradation, to identify problems with pulse generator operation, and/or to control pulse generator operation for improved performance. The pulse generator may also be configured and controlled to generate a high-voltage initiation pulse to initiate a subsequent discharge pulse while being contained within a relatively small form factor. The pulse generator may be used in spectroscopy systems or other systems using high voltage discharge pulses.

12 Claims, 6 Drawing Sheets

Related U.S. Application Data

(60) Provisional application No. 61/363,733, filed on Jul. 13, 2010.

(51) Int. Cl.
  | | |
  |---|---|
  | *H05H 1/46* | (2006.01) |
  | *G01J 3/02* | (2006.01) |
  | *G01J 3/443* | (2006.01) |
  | *H01J 37/32* | (2006.01) |
  | *G01N 21/67* | (2006.01) |

(52) U.S. Cl.
  CPC .......... *H05K 9/0037* (2013.01); *G01N 21/67* (2013.01); *H01J 37/32055* (2013.01); *H05H 2001/4682* (2013.01)

(56) References Cited

U.S. PATENT DOCUMENTS

| | | | |
|---|---|---|---|
| 2,735,330 A | 2/1956 | Polster | |
| 3,093,770 A | 6/1963 | Wesley et al. | |
| 3,141,111 A | 7/1964 | Godlove | |
| 3,247,887 A | 4/1966 | Matthews | |
| 3,248,602 A | 4/1966 | Irish et al. | |
| 3,308,339 A | 3/1967 | Berneron | |
| 3,349,284 A | 10/1967 | Roberts | |
| 3,567,993 A | 3/1971 | Sturm | |
| 3,749,975 A | 7/1973 | Walters | |
| 3,806,305 A | 4/1974 | Dietz et al. | |
| 3,900,786 A | 8/1975 | Jordan | |
| 3,906,291 A | 9/1975 | Schayes et al. | |
| 3,973,167 A | 8/1976 | Walters et al. | |
| 4,055,783 A | 10/1977 | Walters et al. | |
| 4,069,801 A | 1/1978 | Stevens | |
| 4,182,574 A | 1/1980 | Quillfeldt | |
| 4,203,052 A | 5/1980 | Bechtel | |
| 4,296,358 A | 10/1981 | Bernier | |
| 4,393,327 A | 7/1983 | Walters et al. | |
| 4,541,848 A | 9/1985 | Masuda | |
| 4,629,887 A | 12/1986 | Bernier | |
| 4,641,968 A * | 2/1987 | Grandy ............... G01N 21/67 |
| | | | 315/209 CD |
| 4,716,342 A | 12/1987 | Mccaffrey | |
| 4,723,438 A | 2/1988 | Adler-Golden et al. | |
| 4,766,318 A | 8/1988 | Adler-Golden et al. | |
| RE32,911 E | 4/1989 | Walters | |
| 4,993,834 A | 2/1991 | Carlhoff et al. | |
| 4,995,723 A | 2/1991 | Carlhoff et al. | |
| 5,085,499 A | 2/1992 | Griffin et al. | |
| 5,153,519 A * | 10/1992 | Wentworth ............ G01N 27/70 |
| | | | 324/123 R |
| 5,155,547 A | 10/1992 | Casper et al. | |
| 5,215,066 A | 6/1993 | Narishige et al. | |
| 5,216,482 A | 6/1993 | Fukui et al. | |
| 5,221,349 A * | 6/1993 | Tamagaki ............. C23C 14/325 |
| | | | 118/708 |
| 5,245,406 A | 9/1993 | Masutani | |
| 5,285,251 A | 2/1994 | Pilloud et al. | |
| 5,399,910 A | 3/1995 | Lamain et al. | |
| 5,406,166 A | 4/1995 | Abe et al. | |
| 5,446,538 A | 8/1995 | Noll | |
| 5,486,993 A * | 1/1996 | Sakurai ............. H02M 7/53871 |
| | | | 363/137 |
| 5,777,867 A * | 7/1998 | Hongu ................. G02B 6/2551 |
| | | | 361/257 |
| 5,847,825 A | 12/1998 | Alexander | |
| 5,991,355 A | 11/1999 | Dahlke | |
| 6,034,768 A | 3/2000 | Fraser et al. | |
| 6,114,842 A | 9/2000 | Simpson et al. | |
| 6,662,793 B1 | 12/2003 | Allen et al. | |
| 6,806,628 B2 | 10/2004 | Suzuki | |
| 6,999,295 B2 | 2/2006 | Watkins, III et al. | |
| 7,010,386 B2 | 3/2006 | Mcdonnell et al. | |
| 7,120,220 B2 | 10/2006 | Du et al. | |
| 7,121,270 B1 | 10/2006 | Plotnikov | |
| 7,145,762 B2 | 12/2006 | Nerheim | |
| 7,209,373 B2 | 4/2007 | Oicles et al. | |
| 7,221,977 B1 | 5/2007 | Weaver et al. | |
| 7,318,889 B2 | 1/2008 | Dowling | |
| 7,330,025 B1 | 2/2008 | Beach et al. | |
| 7,391,508 B2 | 6/2008 | Grodzins | |
| 7,457,096 B2 | 11/2008 | Brundula | |
| 7,515,263 B2 | 4/2009 | Kwon et al. | |
| 7,525,653 B1 | 4/2009 | Hug et al. | |
| 7,530,265 B2 | 5/2009 | Difoggio | |
| 7,565,267 B2 | 7/2009 | Warizaya | |
| 7,570,476 B2 * | 8/2009 | Nerheim ............. F41H 13/0012 |
| | | | 361/232 |
| 7,582,842 B2 | 9/2009 | D'Amario | |
| 7,610,174 B2 | 10/2009 | Rosner et al. | |
| 7,782,592 B2 | 8/2010 | Nerheim | |
| 7,821,766 B2 | 10/2010 | Brundula | |
| 7,936,552 B2 | 5/2011 | Nerheim | |
| 2003/0103137 A1 * | 6/2003 | Espertshuber ....... G01R 31/311 |
| | | | 348/87 |
| 2007/0247621 A1 | 10/2007 | Kawato | |
| 2008/0259330 A1 * | 10/2008 | Dillon ..................... G01J 3/02 |
| | | | 356/318 |
| 2010/0061034 A1 * | 3/2010 | Kaplan ................... F23Q 3/004 |
| | | | 361/256 |
| 2012/0285620 A1 * | 11/2012 | Larson ............. H01J 37/32944 |
| | | | 156/345.28 |

OTHER PUBLICATIONS

Schrenk, W.G., "Historical Development Of High-Energy Excitation Sources For Analytical Emission Spectroscopy", Applied Spectroscopy, 1988, pp. 4-11, vol. 42, No. 1.

Cousins, Jennifer Cappel; Scheeline, Alexander and Coleman, David M., "High-Voltage Spark Spectra: Utility As A Function Of Temporal And Spatial Resolution", Applied Spectroscopy, 1987, pp. 954-962, vol. 41, No. 6.

Perkin-Elmer, "TR-2081 External Trigger Transformer", optoelectronics. perkinelmer.com, 2004, PerkinElmer, Inc.

\* cited by examiner

PULSE GENERATOR AND SYSTEMS AND METHODS FOR USING SAME

CROSS-REFERENCE TO RELATED APPLICATIONS

The present application is a divisional of U.S. patent application Ser. No. 13/181,745 filed Jul. 13, 2011, which claims the benefit of U.S. Provisional Patent Application Ser. No. 61/363,733 filed Jul. 13, 2010, all of which are fully incorporated herein by reference.

TECHNICAL FIELD

The present invention relates to pulse generators and more particularly, to a pulse generator for generating electrical discharge pulses such as spark or plasma discharges.

BACKGROUND INFORMATION

High voltage pulse generators have been used to generate discharge pulses, such as spark and/or plasma discharges, between electrodes attached to the pulse generator. In one application, a high voltage pulse generator has been used in spark induced breakdown spectroscopy (SIBS) based instruments. In some SIBS instruments, an intense electrical discharge between two electrodes creates plasma from the gas flowing between the electrodes, where the gas may include aerosolized particles of interest. Optical detectors then measure properties of the resulting plasma with the aim of quantifying the identities and concentrations of the aerosolized particles. Examples of SIBS and other similar spectroscopy techniques are described, for example, in the article entitled "Historical Advances in Spark Emission Spectroscopy" by J. P. Walters, Volume 23, Number 4, 1969, *Applied Spectroscopy*, in the article entitled "Preliminary correlations of feature strength in spark-induced breakdown spectroscopy of bioaerosols with concentrations measured in laboratory analyses" by M. S. Schmidt and A. J. R. Bauer, Volume 49, Number 13, 2010, *Applied Optics*, and in U.S. Pat. Nos. 3,749,975, 3,973,167; 4,393,327; 4,766,318; and 6,034,768, all of which are fully incorporated herein by reference. Other applications for pulse generators include spark plugs, underwater acoustics, stun guns, and explosive discharges as described in U.S. Pat. Nos. 3,093,770; 5,215, 066; and 6,999,295.

One problem that arises in devices that produce electrically induced spark and/or plasma discharges between electrodes is the degradation of the electrodes. The electrodes may be deformed and eroded continuously as pulses are passed through them until eventually the electrodes are no longer useful and must be replaced. Some existing devices have attempted to address this problem by using robust materials for the electrodes. In other existing devices, one of the electrodes is made from the material to be analyzed and is thus eroded as it is analyzed. High voltage pulse generators may also include other power circuitry elements that tend to wear out with extended use.

When electrodes and/or other components are susceptible to degradation or failure with extended use, existing methods for monitoring usage have been inadequate to determine when such electrodes or components should be replaced. As a result, the devices (e.g., SIBS instruments or spark plugs) in which the pulse generators are used may degrade or even stop functioning unexpectedly and without warning.

Another problem that arises is the unique challenge of designing a high voltage pulse generator with a small enough form factor to be viable, for example, for field portable applications. Providing high voltage circuitry capable of generating discharge pulses of sufficiently high pulse energy and frequency within a small space often leads to malfunctions of the power circuitry elements and/or control circuitry. To generate an electrical discharge pulse, some existing pulse generators discharge a charged capacitor into the primary side of a high voltage step-up transformer such that a corresponding high voltage pulse is generated at the secondary side of the transformer. The ability to decrease the size of a pulse generator using this existing circuit design is limited. High voltage pulse generators may also be required to meet certain electro-magnetic interference and compatibility (EMI/EMC) and environmental requirements.

BRIEF DESCRIPTION OF THE DRAWINGS

These and other features and advantages will be better understood by reading the following detailed description, taken together with the drawings wherein.

DETAILED DESCRIPTION

In general, a pulse generator, consistent with embodiments described herein, generates high voltage discharge pulses in a manner that may be controlled and monitored. Pulse generator operation may be monitored to measure characteristics associated with pulse generator operation and to produce pulse generator data representative of those characteristics. Pulse generator operation may be monitored by monitoring the discharge pulses produced by the pulse generator and/or the charging of energy storage elements within the pulse generator in preparation for a subsequent discharge pulse. The pulse generator data may be used, for example, to identify pulse generator wear or degradation, to identify problems with pulse generator operation, and/or to control pulse generator operation for improved performance.

In other embodiments, the pulse generator may be configured and controlled to generate a high-voltage initiation pulse to initiate a subsequent high energy discharge pulse while being contained within a relatively small form factor. As used herein, "high voltage" refers to a voltage that is high relative to an input voltage to the pulse generator and sufficiently high to generate or sustain an electrical discharge pulse, as described in greater detail below. In further embodiments, the pulse generator may provide electromagnetic interference (EMI) shielding and other structural features that enable controllable discharge pulse circuitry in a relatively small form factor. Embodiments of the pulse generator may be used in spectroscopy systems or other systems using high voltage discharge pulses.

Figure 1:
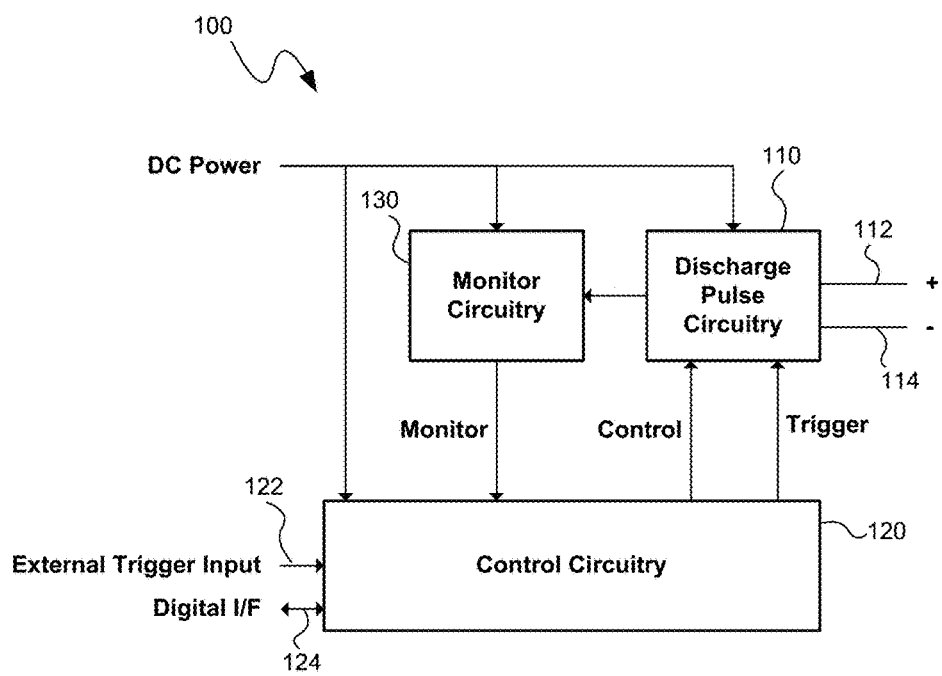
FIG. 1 is a schematic block diagram of a pulse generator consistent with an embodiment of the present disclosure.

Referring to FIG. 1, a pulse generator 100 generally includes discharge pulse circuitry 110 and control circuitry 120. In general, the discharge pulse circuitry 110 charges and discharges for generating electrical discharge pulses and the control circuitry 120 controls the charging and generation of discharge pulses in the discharge pulse circuitry 110. The control circuitry 120 controls characteristics of discharge pulse generation such as, for example, the pulse energy and the timing or triggering of the discharge pulses. The pulse generator 100 may also include monitor circuitry 130 that measures characteristics of pulse generator operation such as discharge pulse characteristics and/or charging characteristics. The control circuitry 120 may collect measurements from the monitor circuitry 130 to produce pulse generator data representative of the measured characteristics. Pulse generator data may include discharge pulse data representative of discharge pulse characteristics quantifying discharge pulses (e.g., a pulse magnitude, a pulse duration, a pulse delay relative to a trigger, a pulse count, and a cumulative magnitude of discharge pulses) and charging characteristic data representative of measured charging characteristics (e.g., a charge rate and/or stored energy level). The monitor circuitry 130 may generate signal level representations of the various measured characteristics of pulse generator operation, which may be fed back to the control circuitry 120 for real-time monitoring and control of the charging and generation of discharge pulses and for tracking the pulse generator data.

The discharge pulse circuitry 110 may generate relatively high power electrical discharge pulses from relatively low voltage input power supplied to the pulse generator 100. The input power is generally DC in nature but AC input power sources may also be used. In one example, the pulse generator 100 is capable of generating discharge pulses with a pulse energy in a range of about 0.05 to 0.5 Joules per pulse, a pulse energy resolution of ≤0.05 Joules, a pulse energy duration of ≤30 microseconds, a minimum time between sequential pulses of ≤50 milliseconds (e.g., a pulse frequency of ≤20 Hz), and an input power of 10 to 15 Volts D.C. The concepts described herein may also be used in pulse generators having other operating parameters or characteristics.

Figure 1A:
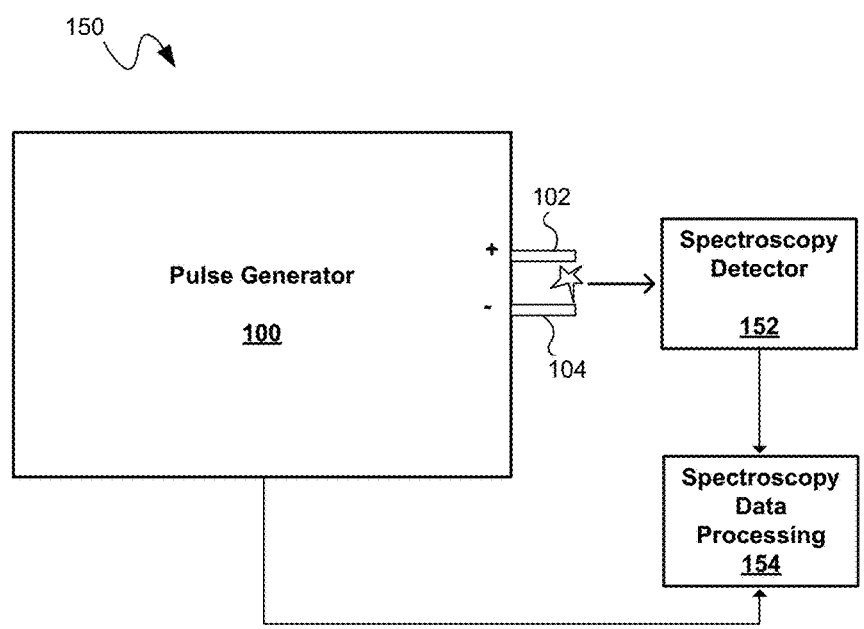
FIG. 1A is a schematic block diagram of a spectroscopy system including a pulse generator consistent with an embodiment of the present disclosure.

The discharge pulse circuitry 110 also includes leads 112, 114 for coupling to electrodes (not shown in FIG. 1). Each discharge pulse generated by the discharge pulse circuitry 110 causes a spark and/or plasma discharge across the electrodes coupled to the leads 112, 114. The combined assembly of the pulse generator 100 and electrodes may be used in another apparatus or system. As shown in FIG. 1A, for example, the pulse generator 100 may be used as a sub-component in a spectroscopy system 150, such as a SIBS instrument. The spectroscopy system 150 further includes a spectroscopy detector 152 with optical detectors that detect spectroscopic emissions resulting from electrical discharge pulses generated between electrodes 102, 104 coupled to the leads of the pulse generator 100. The spectroscopy detector 152 may also produce data representative of the detected spectroscopic emissions. In other applications, the pulse generator 100 may be used in other systems such as a spark plug system.

The spectroscopy system 150 may also include spectroscopy data processing circuitry 154 either locally coupled or remotely coupled to the spectroscopy detector 152. Remotely coupled spectroscopy data processing circuitry 154 may include an external computer system. The spectroscopy data processing circuitry 154 may process spectroscopic emissions data produced by the spectroscopy detector 152, for example, to conduct further analysis of the spectroscopic emissions. The spectroscopy data processing circuitry 154 may also receive pulse generator data from the pulse generator 100 and may correlate the spectroscopic emissions data with the pulse generator data that produced the emissions, for example, in connection with analysis of the spectroscopic emissions data.

The control circuitry 120 may include an external trigger input 122 to receive external trigger control signals. The control circuitry 120 may also generate an internal trigger signal to serve as a proxy for configurations in which no external trigger is present. The control circuitry 120 may further include a digital interface 124 to provide communication with an external device or system. The digital interface 124 may receive, for example, control signals (e.g., to adjust pulse energy) from an external control device. The digital interface 124 may also provide pulse generator data or other data to an external system or device. The data exchange may also be provided using an analog interface and signals.

As used in any embodiment herein, "circuit" and "circuitry" may include, for example, singly or in any combination, analog circuitry, digital circuitry, hardwired circuitry, programmable circuitry such as a microcontroller, programmable logic (CPLD, FPGA, etc.), state machine circuitry, and/or firmware that stores instructions executed by programmable circuitry. "Integrated circuit", as used in any embodiment herein, may include a circuit or circuitry in the form of a semiconductor device and/or microelectronic device, such as, for example, a semiconductor integrated circuit chip. The control circuitry 120 may be implemented as any circuit or circuitry, including an integrated circuit, configured to perform the control functions described herein. Those skilled in the art will recognize various implementations for the control circuitry including any combination of hardware, software and firmware that is configured or programmed to perform the functions described herein. Although the illustrated embodiments show discrete blocks representing circuitry that performs various functions of the pulse generator, the circuitry is not necessarily located in a discrete unit and the arrangement of the circuitry is not intended to be a limitation of the present invention.

Figure 2:
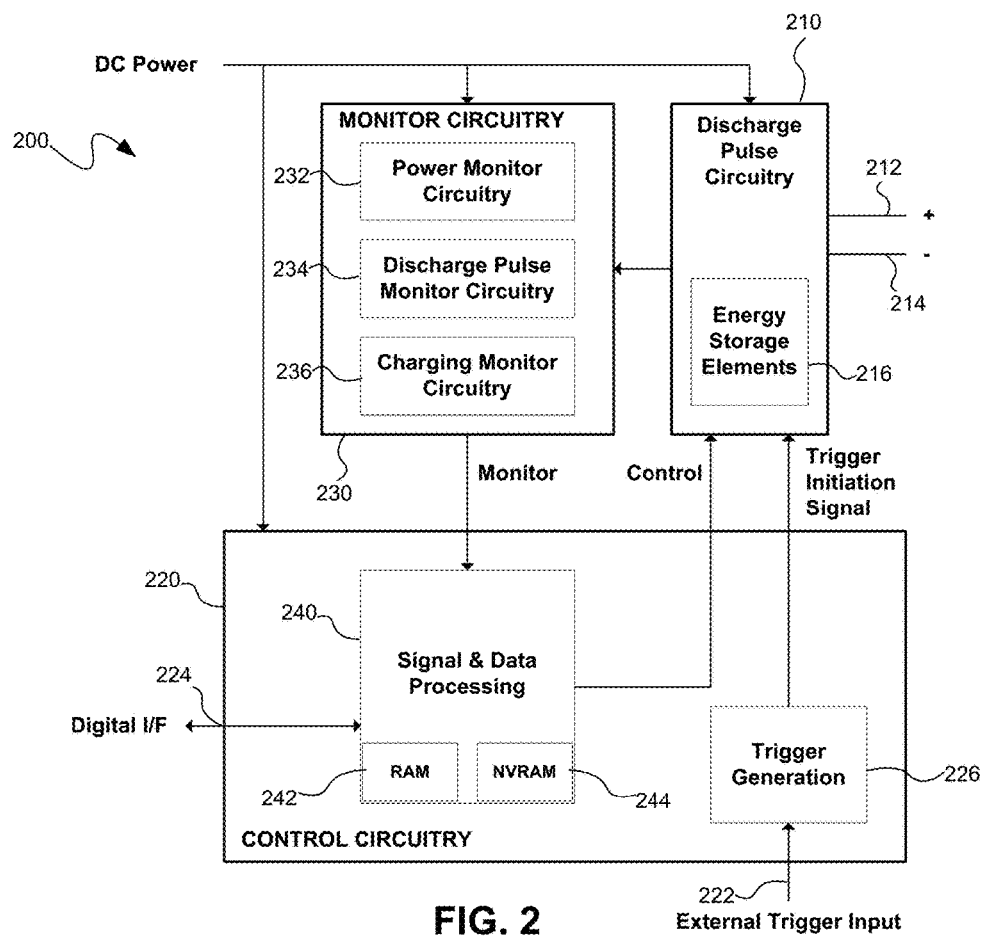
FIG. 2 is a schematic block diagram of a pulse generator consistent with another embodiment of the present disclosure.

Referring to FIG. 2, another embodiment of a pulse generator 200 including discharge pulse circuitry 210, control circuitry 220, and monitor circuitry 230 is shown and described in greater detail. In this embodiment, the control circuitry 220 includes trigger generation circuitry 226 that generates a trigger initiation signal, for example, in response to an external trigger input 222. Prior to the receipt of the external trigger input 222, the control circuitry 220 controls the charging of energy storage elements 216 within the discharge pulse circuitry 210 and maintains this energy until the receipt of the external trigger. Since a pre-stored quantity of energy is available within the discharge pulse circuitry 210 at the moment the control circuitry 220 receives the trigger, the control circuitry 220 may be configured to cause the immediate generation of a high-voltage initiation pulse followed by one or more discharge pulses in quick succession. In a spectroscopy application, the control circuitry 220 may also generate a synchronization signal, transmitted by means of a digital interface 224, for use in triggering external optical detectors with maximum timing precision with respect to the generation of the discharge pulse.

The illustrated embodiment of the control circuitry 220 also includes signal and data processing circuitry 240 that receives and processes data associated with pulse generator operation. The signal and data processing circuitry 240 is coupled to the digital interface 224 to receive control signals such as pulse energy control signals and to provide data such as pulse generator data. The signal and data processing circuitry 240 may include memory such as volatile memory 242 and non-volatile memory 244 to store data such as pulse generator data and/or other data (e.g., serial number and configuration information) related to the pulse generator. In one embodiment, the signal and data processing circuitry 240 may be implemented as a microcontroller with firmware stored in the non-volatile memory 244.

The non-volatile memory 244 may include, without limitation, non-volatile random access memory (NVRAM), electrically-erasable programmable read-only memory (EE-PROM), and/or flash memory. The volatile memory 242 may include, without limitation, random access memory (RAM) such as dynamic random access memory (DRAM) and/or static random access memory (SRAM). In other embodiments, the signal and data processing circuitry 240 may include only non-volatile memory such as RAM that is inherently non-volatile and capable of storing data both for processing during operation and for persistent storage after being powered down. The digital interface 224 may include a standard control signal interface such as RS-232, USB, Ethernet, CAN, or other such interfaces. The external trigger input 222 may include any standard, either single-ended or differential, logic input such as a TTL compatible input or a CMOS logic input. Signal transformers or optoisolators may also be used to receive the trigger.

In the illustrated embodiment, the monitor circuitry 230 includes power monitor circuitry 232, discharge pulse monitor circuitry 234 and charging monitor circuitry 236. The power monitor circuitry 232 monitors the input power supply voltage to detect the onset of a power fail condition. The discharge pulse monitor circuitry 234 monitors the discharge pulses generated by the discharge pulse circuitry 210 and discharged through the leads 212, 214 to measure characteristics of the discharge pulses, such as the occurrence of a pulse, a magnitude of a pulse (e.g., the electrical discharge energy level), a pulse duration, a pulse delay relative to a trigger, and/or the voltage amplitude of a high-voltage initiation pulse used to generate the discharge pulse. The charging monitor circuitry 236 monitors the charging of the internal energy storage elements within the discharge pulse circuitry to measure charging characteristics, such as charge rate or energy storage level.

The signal and data processing circuitry 240 may collect measurements from any one of the power monitor circuitry 232, discharge pulse monitor circuitry 234 and charging monitor circuitry 236 and may produce, process and store pulse generator data representative of the measured characteristics. The signal and data processing circuitry 240 may also report the pulse generator data to a user (e.g., through digital interface 224) and/or provide indications of certain conditions of the pulse generator 200 to the user based on the pulse generator data. The signal and data processing circuitry 240 may further control operation of the discharge pulse circuitry 210 in response to the pulse generator data.

With respect to discharge pulse characteristics, the signal and data processing circuitry 240 may produce discharge pulse data representative of characteristics quantifying accumulated discharge pulses as measured by the discharge pulse monitor circuitry 234. The discharge pulse data may include, without limitation, a discharge pulse count or number of electrical discharge pulses that are discharged through the leads 212, 214, a pulse magnitude of each discharge pulse generated, an accumulated magnitude of the discharge pulses generated, an amplitude of the high-voltage initiation pulse used to generate the discharge pulse and/or any other data quantifying the discharge pulses. The accumulated or cumulative magnitude of the discharge pulses may be calculated, for example, as a sum of the magnitude (e.g., the electrical discharge energy level) of each of the discharge pulses that are counted. The magnitude of the discharge pulses may be represented by a number of metrics of the pulse such as energy, peak power, integrated current, peak current, integrated optical intensity, peak optical intensity, and other such metrics related to the overall, average, or peak intensity of the discharge pulse. The commanded pulse magnitude may be used in lieu of, or in addition to, the measured pulse magnitude in the discharge pulse data.

Discharge pulse data (and other pulse generator data) may be stored for the lifetime of the pulse generator 200 and/or for one or more sub-intervals of the lifetime of the generator 200 (e.g., corresponding to the electrodes coupled to the generator or some other component within or coupled to the generator). The lifetime pulse generator data may persist without being resettable and the interval pulse generation data may be resettable (e.g., reset to 0) prior to the start of another sub-interval. The interval pulse generator data may be reset, for example, when new electrodes are connected to the leads 212, 214 of the pulse generator 200 to track the generator pulse activity for a particular set of electrodes. The interval pulse generator data may thus be used to determine when a particular set of electrodes should be replaced. The lifetime pulse generator data may be used to determine the degree of stress on certain power circuitry elements that tend to wear out with extended use over the course of the lifetime of the pulse generator and thus may allow estimates of the remaining useful operational life for a given pulse generator. Tracking pulse generator data thus facilitates maintenance of any apparatus or system in which the pulse generator is used.

Discharge pulse data (both lifetime and interval) representing the magnitudes of the pulses may also be stored as a histogram of the magnitudes of the discharge pulses. The signal and data processing circuitry 240 may sort the magnitudes of the discharge pulses into memory locations or registers corresponding to histogram bins associated with magnitudes or energy levels. A number of different unique sets of energy bins may be used; for example, the bins may be linearly related or logarithmically related. The pulse generation histogram data may thus allow for maintenance of the electrodes or for estimates of the remaining operational life of the generator based on a different criteria other than a simple count of pulses or the total accumulated energy of pulses.

In a further embodiment, discharge pulse data (both lifetime and interval) representing magnitudes of the pulses, counts of the pulses, and any other discharge pulse characteristics or functions thereof may be processed (e.g., using algorithms) to determine maintenance or replacement schedules for the pulse generator or for electrodes attached to the pulse generator. One such algorithm that produces calculated data as a function of monitored values is the generation of statistical metrics such as mean and standard deviation values derived from historical discharge pulse magnitudes. Determination of the maintenance schedule for the electrodes attached to the pulse generator can be improved through tracking changes in such statistical metrics.

The discharge pulse data may also be processed by data processing circuitry located either internal to the pulse generator or external to the pulse generator (e.g., in a computer) to adjust an operating parameter in response to the discharge pulse data, thereby improving or enhancing performance. As electrodes degrade (e.g., as indicated by the discharge pulse data), for example, a higher voltage may be needed to initiate the discharge pulse across the electrodes. A pulse initiation control parameter may be increased in response to a calculated decrease in the probability of a discharge pulse as represented by the discharge pulse data. Thus, the pulse generator may initially use only the initiation voltage that is needed for the discharge pulses and the control parameter that sets the initiation voltage may be adjusted accordingly in response to discharge pulse data indicative of degradation. Other pulse initiation control parameters may similarly be adjusted in response to discharge pulse data.

Tracking discharge pulse data (e.g., pulse counts or accumulated magnitude data) is particularly advantageous in a system in which pulses are not periodic and predictable. When the pulses are not predictable, it is difficult to estimate the approximate number of pulses based on the operational time of the generator and thus the operational time may not be a useful indicator of component wear.

In addition to or instead of discharge pulse data representative of accumulated discharge pulses, the signal and data processing circuitry 240 may also produce and store discharge pulse data on a pulse-by-pulse basis such as pulse magnitude, pulse duration or width, pulse delay relative to a trigger, and other data representing characteristics of individual discharge pulses as they occur. Tracking discharge pulse data on a pulse-by-pulse basis enables additional monitoring and control of pulse generator operation and/or analysis of data produced by a system, such as a spectroscopy system, in which the pulse generator is used, as will be described below.

With respect to charging characteristics, the signal and data processing circuitry 240 may produce charging characteristic data representative of charging characteristics as measured by the charging monitor circuitry 236. Charging characteristic data may include, without limitation, a rate of charge build up in the energy storage elements, a stored energy level in the energy storage elements, a level of completion of the charge process, and any other data representing a charging characteristic. The charging characteristic data may be used, for example, to modify or halt pulse generator operation or to service the pulse generator.

To measure a rate of charge, the charging monitor circuitry 236 can monitor the process of charging one or more internal energy storage elements that provide the instantaneous energy for the discharge pulses. In cases where an electrical component within the pulse generator 200 has degraded or where the electrodes connected to the leads 212, 214 have unintentionally shorted together, the rate of charge build-up on the internal pulse generator energy storage elements may be affected and may be indicative of a problem. A comparison of the measured charge rate to an expected target charge rate can produce charge characteristic data indicating the need for maintenance of the pulse generator or its corresponding electrodes. The signal and data processing circuitry 240 may determine if the measured charge rate varies from a specified target charge rate by more than an allowable deviation, for example, by comparing the measured target rate to the sum of the target charge rate and the allowable deviation.

To measure energy storage level, the charging monitor circuitry 234 can monitor the discharge pulse circuitry 210 after any energy storage elements within the discharge pulse circuitry 210 have been fully charged but prior to generation of the discharge pulse. A comparison of a measured energy storage level with an expected energy storage level can produce additional charging characteristic data indicating unexpected changes in the magnitude of stored energy and a potential problem with the pulse generator. The signal and data processing circuitry 240 may determine if the measured stored energy level varies from a specified target energy level by more than an allowable deviation, for example, by comparing the measured stored energy level to the sum of the target energy level and the allowable deviation. Based on this measurement, the signal and data processing circuitry 240 may take immediate actions to correct the stored energy to a level within the allowable deviation.

Charging characteristic data, such as charge rate, may also be used to minimize the input current draw from the external power supply so as to present the most benign load possible to that external power source. If additional time is allowed to charge the energy storage elements, the charge rate of those elements may be reduced, thereby reducing the input current draw to the unit. If the measured charge rate increases (e.g., if the external power supply voltage increases) as represented by the charge rate data, the control circuitry 220 may reduce the charge rate back to the intended level, thereby reducing the input current draw of the pulse generator.

Monitoring of the charging process can also be used to achieve more precise control over the magnitude of stored energy. By providing charging characteristic data representing the level of completion of the charging process, for example, the control circuitry 220 may charge the internal energy storage elements at a faster rate for the majority of the charging time but at a slower rate towards the end of the charging process. As a result, the control circuitry 220 achieves a fast overall charge time but is presented with lower energy uncertainty per unit time when terminating the charging process than would have resulted at the faster charge rate.

The control circuitry 220 may store at least a subset of the pulse generator data (i.e., discharge pulse data and/or charging characteristic data) temporarily in the volatile memory 242 and persistently in the non-volatile memory 244. In one embodiment, the pulse generator data may be stored and manipulated in the volatile memory 242 during the time that the generator is operating. The pulse generator data may be written to the non-volatile memory 244 on a periodic basis during operation and/or upon power-down. Periodically writing data to the non-volatile memory may reduce the amount of the data that is lost if power is removed without warning. Writing data to the non-volatile memory only upon power-down may extend the lifetime of the non-volatile memory 244, such as an EEPROM, by limiting the number of write cycles. In one embodiment, the power monitor circuitry 232 notifies the signal and data processing circuitry 240 of a low voltage power condition, allowing the signal and data processing circuitry 240 to write the pulse generator data to the non-volatile memory 244 immediately prior to power-down. In each case, the control circuitry 220 reads the pulse generator data from the non-volatile memory 244 after power-up and writes the data to volatile memory 242 prior to the start of discharge pulse generation. The control circuitry 220 may also clear at least a subset of the pulse generator data (e.g., the interval data) from the storage locations in the non-volatile memory 244, for example, in response to user input.

Figure 3:
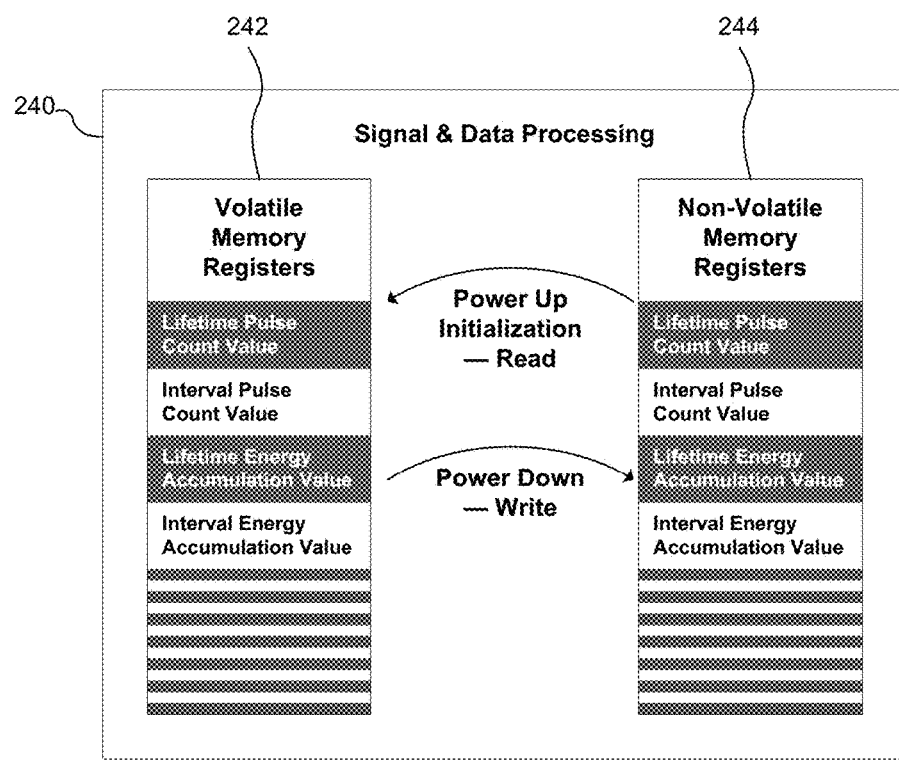
FIG. 3 is a functional block diagram illustrating a storage process including a counter and accumulator function in a pulse generator consistent with an embodiment of the present disclosure.

FIG. 3 illustrates one example of the storage of discharge pulse data by the signal and data processing circuitry 240, consistent with one embodiment. The volatile memory 242 may include memory registers for storing a lifetime pulse count value, an interval pulse count value, a lifetime energy accumulation value, and an interval energy accumulation value. The non-volatile memory 244 may similarly include memory registers for storing a lifetime pulse count value, an interval pulse count value, a lifetime energy accumulation value, and an interval energy accumulation value. Upon power up and initialization, the data values are read from the non-volatile memory registers into the volatile registers. Upon power down, the data values are written from the volatile memory registers to the non-volatile memory registers. Although the illustrated embodiment refers to only one interval, multiple interval values may be stored for each of the types of discharge pulse data over multiple sub-intervals (e.g., corresponding to different components).

The signal and data processing circuitry 240 may also perform an error checking function after writing to the non-volatile memory 244. As part of the power-down sequence, for example, the signal and data processing circuitry 240 may compare written contents of the non-volatile memory 244 with the corresponding contents of the volatile memory 242 in order to detect a failure of the storage process and take corrective action in response thereto. The corrective action may include, without limitation, a repeated attempt to store the pulse generator data to the same location, storage of the data to a different location, and disabling the location where the failure occurred. If the written contents of a memory register in the non-volatile memory 242 do not match the corresponding contents of the volatile memory 244, for example, the signal and data processing circuitry 240 may deem that particular memory register in the non-volatile memory 242 as bad and may index to another physical memory register to store the data record. The error checking function may thus further extend the useful life of non-volatile memory having a limited number of write cycles.

As mentioned above, the signal and data processing circuitry 240 may also include operational memory technology that is inherently non-volatile. In these embodiments, the signal and data processing circuitry 240 may store the pulse generator data without control processes for the preservation and restoration of the data at power-down and power-up, and the storage function may be achieved by configuring the control circuitry to prevent initialization of the pulse generator data memory locations after power-up.

In another embodiment, an external discharge pulse monitor (not shown) may be used to track the signals (e.g., the trigger signals and pulse energy control signals) provided to the pulse generator 200. The external discharge pulse monitor may be implemented, for example, on a computer system that communicates with the pulse generator 200 through the digital interface 224. In further embodiments, the pulse generator 200 may be coupled to or incorporated into a system with non-volatile storage located external to the pulse generator 200. This can be advantageous in situations where the pulse generator data is one of a number of data sets that are stored over long periods of time. The data may be reported to the external system for storage on a pulse-by-pulse basis or on a less frequent, summarized basis either in response to a command requesting such data or automatically. The externally stored data may be used in the same way as internally stored data described above. In some embodiments, a significant portion of the pulse generator data may be maintained within the pulse generator 200 and only a limited subset of the data will be reported to the external system and stored outside the pulse generator 200. Maintaining the pulse generator data (and particularly the lifetime data) within the pulse generator 200 provides less of an opportunity for the pulse generation data to become disassociated from a given pulse generator or from a given set of electrodes or some other component coupled to the generator.

Pulse generator data may also be reported by and/or transmitted from the control circuitry 220 by means of the digital interface 224 for other purposes. Pulse generator data may be reported and/or transmitted, for example, on a pulse-by-pulse basis immediately following the initiation or generation of individual discharge pulses, in response to a user command, and/or automatically (e.g., periodically or when values of the data fall within or outside a predefined range). External pulse generator data reports may be used for the detection of out-of-range values of the discharge pulse magnitude that might result in mitigation actions or immediate termination of pulse generator operation. External pulse generator data reports may also be used to correlate pulse generator data with corresponding spectroscopy data collected externally to normalize the associated spectroscopy data magnitudes as well as to tag or filter out spectroscopic data from non-compliant discharge pulses. A non-compliant pulse is a discharge pulse that does not comply with predefined discharge pulse parameters for a particular application, such as a magnitude or duration within a predefined range. To enable this determination based on received, pulse-by-pulse data reports, the contents of such reports may include monitored values such as the magnitude of the discharge pulse, a representative pulse width such as the full-width-half-maximum pulse duration, a discharge pulse generation delay value relative to a trigger (e.g., the delay from the trigger initiation signal to the peak of the pulse), or an internally derived conclusion regarding the compliance of the pulse and represented as a binary value (i.e., a tag value).

Figure 4:
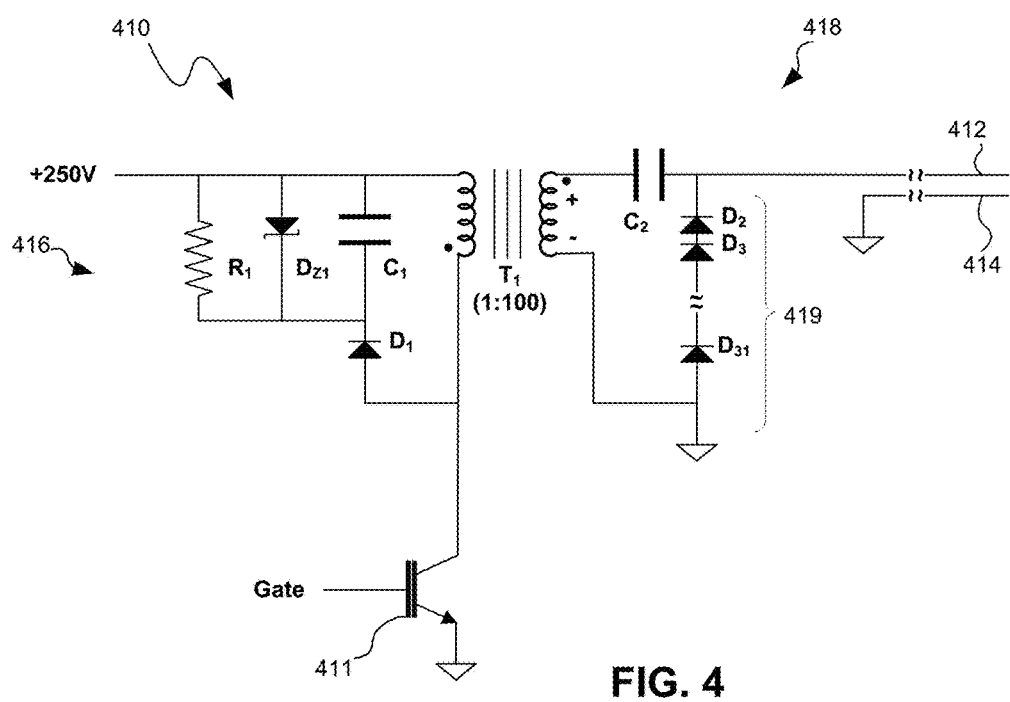
FIG. 4 is a schematic diagram of an embodiment of augmented transformer trigger circuitry that may be used in the discharge pulse circuitry of a pulse generator.

Referring to FIG. 4, another embodiment of a pulse generator may include discharge pulse circuitry with augmented transformer trigger circuitry 410 capable of generating a high-voltage initiation pulse to initiate a subsequent energy discharge pulse. The transformer trigger circuitry 410 generally includes a high-voltage transformer $T_1$ coupled to circuitry 416 on the primary side for charging and switching the transformer $T_1$ and coupled to circuitry 418 on the secondary side for generating the high-voltage initiation pulse that produces the subsequent discharge pulse. The high-voltage initiation pulse is generated by a voltage swing in the secondary-side circuitry 418 after stored energy is released from the transformer $T_1$ when the transformer $T_1$ is switched in response to a trigger initiation signal. The high-voltage initiation pulse occurs after the trigger initiation signal is terminated.

In general, the augmented transformer trigger circuitry 410 of this embodiment generates higher voltages for the high-voltage initiation pulse than might otherwise be generated by the transformer $T_1$ for a given primary-side drive voltage and transformer turns ratio. This augmented high-voltage initiation pulse may be accomplished through a resonance response in the transformer and more generally through the use of energy storage on a transient basis in the transformer $T_1$ and in reactive circuit elements coupled to the transformer $T_1$ during the process of generating the high-voltage initiation pulse. The transformer trigger circuitry 410 of this embodiment and the method described herein is also capable of providing a very short delay from the receipt of a trigger to the generation of the high-voltage initiation pulse with little delay jitter from pulse to pulse. In particular, the time delay between the trigger initiation signal and the high-voltage initiation pulse is on the same order of magnitude as a duration of the discharge pulse that is generated. For example, both the delay and jitter may be as short as about 1 microsecond compared to millisecond levels when using conventional triggering methods, which combine the energy storage charging process with the triggering process through the use of a spark-gap breakdown device.

One embodiment of the primary-side circuitry 416 includes a switch 411, such as a high current, N-type insulated gate bipolar transistor (IGBT) responsive to a gate control signal (e.g., the trigger initiation signal provided by the control circuitry) having a pulse waveform. The pulse waveform has a polarity and time duration in a range to induce a resonance response in the transformer $T_1$, for example, by exciting an energy storage resonance between the trigger transformer $T_1$ and reactive electronic components coupled to the transformer. The desired time duration may be determined relative to the resonant frequency of the transformer $T_1$ coupled with its surrounding primary and secondary reactances, as will be described in greater detail below. One example embodiment of the primary-side circuitry 416 also includes a resistor $R_1$, a zener diode $D_{z1}$, a capacitor $C_1$ and a high current diode $D_1$ coupled to the switch 411 and to the primary side of the transformer $T_1$. One example embodiment of the secondary-side circuitry 418 includes a capacitor $C_2$ and a diode string 419 (e.g., 1 kV low current diodes $D_2, D_3, \ldots D_{31}$) coupled to the secondary side of the transformer $T_1$. The secondary-side circuitry 418 further includes leads or cabling 412, 414 for coupling to the electrodes.

When the switch 411 is closed in response to the gate control signal, the primary side of the transformer $T_1$ is charged (e.g., with 250 V) and the voltage at the secondary side of the transformer $T_1$ goes negative, pulling current through the capacitor $C_2$ and the diode string 419 (e.g., $D_2, D_3, \ldots D_{31}$) within the secondary-side circuitry 418 and building up voltage on the capacitor $C_2$ in a manner controlled by a resonance between the transformer and the capacitor $C_2$. When the switch opens at the falling edge of the gate control signal, the secondary-side voltage is at the peak negative voltage. Opening the switch 411 causes the transformer primary-side voltage to reverse direction and the secondary-side voltage follows accordingly. After the voltage reversal, the secondary-side voltage swings upwards in the positive direction, turning off the diode string 419 ($D_2, D_3, \ldots D_{31}$) and allowing the pulse generator output to swing rapidly upwards as well, coupling the energy to the leads 412, 414. A high voltage breakdown occurs between the electrodes connected to the leads 412, 414, thus enabling a discharge current to flow.

The voltage reversal is caused by energy storage in the transformer core during the period of time when the switch 411 is closed, essentially operating the transformer $T_1$ in a flyback converter mode, and is independent of the resonantly stored energy in the secondary-side capacitor $C_2$. Circuit components coupled to the transformer $T_1$ and the switch 411 in the primary-side circuitry 416 may control the magnitude of the secondary-side voltage swing due to the flyback process occurring in the transformer $T_1$. In the illustrated embodiment, for example, the diode $D_1$ redirects the magnetizing current of the transformer $T_1$ into the capacitor $C_1$ and the resistor $R_1$, with the resulting voltage across the pair clamped by the zener diode $D_{Z1}$. This combination of passive elements allows the voltage across the transformer primary to reverse polarity after the switch is released while protecting the transformer from an over-voltage condition.

In addition to the flyback process occurring in the transformer $T_1$, the energy stored in the secondary-side capacitor $C_2$ is released into the output when the diode string 419 ($D_2, D_3, \ldots D_{31}$) turns off and the pulse generator output voltage swing is supplemented to produce the augmented high-voltage initiation pulse. In other words, the peak voltage generated at a pulse generator output exceeds a peak voltage generated at the transformer secondary winding. Thus, the augmented trigger circuitry and method described herein stores significant energy in either the transformer itself and/or resonantly coupled reactive electronic components to produce a voltage at the pulse generator output that is significantly greater than the product of the primary-side excitation source and the transformer turns ratio. In the illustrated embodiment, the high-voltage initiation pulse produced at the pulse generator output can be as much as twice the voltage rating of the transformer secondary. In other embodiments of the augmented transformer trigger circuitry, other waveforms, reactive circuit components, or methods could be used to apply an excitation to the transformer in order to produce similarly augmented output voltage swings.

As mentioned above, the gate control signal has a pulse waveform that drives the switch 411 to the ON state for a time duration in a range that will induce a resonance response in the transformer $T_1$. This time duration depends on the specific configuration of components used to augment the transformer output voltage swing. In the embodiment described herein, closing the switch for too short an excitation period causes less than maximal energy to be stored and may degrade the magnitude of the output pulse. Closing the switch for too long a period causes various effects which will result in differing outcomes depending on the specific configuration of components coupled to the transformer.

Figure 5:
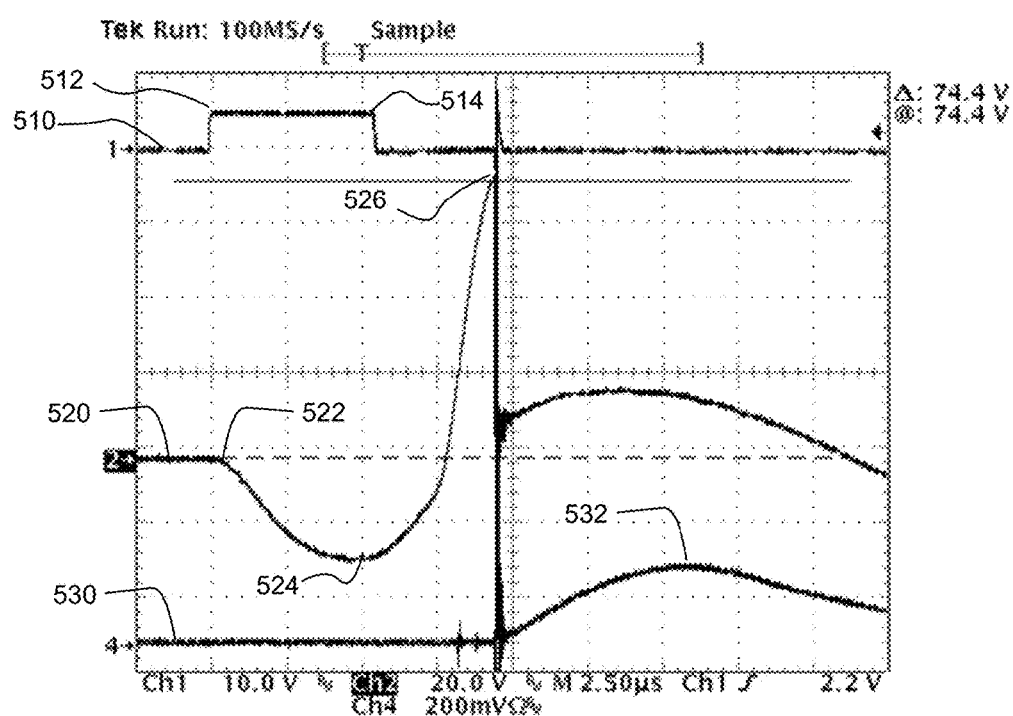
FIG. 5 is an oscilloscope image of a trigger initiation pulse and voltage at a secondary side of a transformer, consistent with one example of operation of an embodiment of the augmented transformer trigger circuitry.

FIG. 5 illustrates one example of a gate control signal, high-voltage initiation pulse, and discharge current on an oscilloscope during a discharge pulse generated by one embodiment of a pulse generator including augmented transformer trigger circuitry. In this illustrated example, channel 1 is the gate control signal 510 where a 5V level corresponds to switching the IGBT transistor to its "ON" or conducting state. Channel 2 is the secondary side voltage waveform 520 from the transformer with a scale factor of approximately 360 Volts per Volt indicating a peak voltage of 26,700 Volts. Channel 4 is the discharge current waveform 530 with a scale factor of approximately 630 mV/kiloAmp indicating a peak current of 350 Amps.

As illustrated, the rising edge 512 of the gate control signal 510 causes the switch 411 to close and corresponds to a negative movement 522 of the secondary-side voltage waveform 520. The falling edge 514 of the gate control signal 510 causes the switch 411 to open and corresponds approximately to the negative voltage peak 524 of the secondary-side voltage waveform 520. After the switch 411 is open, the secondary-side voltage waveform 520 swings from the negative voltage peak 524 in the positive direction until a voltage breakdown 526 occurs, causing the discharge pulse 532.

Accordingly, the augmented transformer trigger circuitry 410 allows the use of a smaller, lower voltage rated transformer to produce the ionization voltage for the generator, thereby enabling smaller pulse generators. FIGS. 4 and 5 merely represent one example of the augmented transformer trigger circuitry and the operation thereof. Other circuitry configurations and drive parameters may also be used to provide flyback mode operation, resonance responses and corresponding augmented voltage swings.

As mentioned above, the discharge pulse circuitry may also be configured to generate multiple discharge pulses following a single high-voltage initiation pulse. In this embodiment, the augmented transformer trigger circuitry may include, for each additional discharge pulse, an energy storage element such as a capacitor used with a series-connected switch to enable its discharge into the output load.

Figure 6:
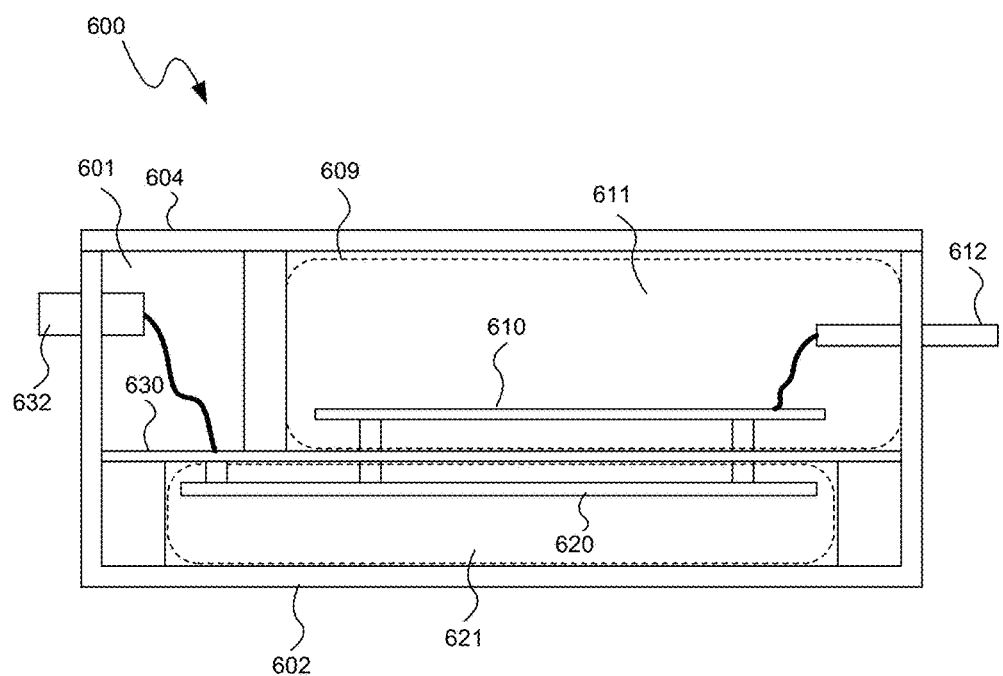
FIG. 6 is a schematic diagram of an embodiment of a pulse generator inside of a pulse generator housing.

Referring to FIG. 6, a pulse generator 600 may be enclosed in a housing 602 that provides EMI shielded chambers for one or more of the circuits. The housing 602 may include a removable cover 604 and may be made of a material capable of providing EMI shielding, such as aluminum. The housing 602 may further include a port for receiving input power and data connector(s) 632 and a port for the leads 612 that are coupled to the electrodes. In one embodiment, a discharge pulse circuit board 610 may be located in a first chamber 611, a control circuit board 620 may be located in a second chamber 621, and the input power and data connectors 632 may be isolated by a third chamber 601. A shield circuit board 630 may form the chambers 601, 611, 621 and may provide isolated electrical connections between the circuit boards. Cabling may be provided from connectors 632 to the shield board 630, which connects to the control circuit board 620. The control circuit board 620 may thus be EMI isolated using the shield board 630 and filtering elements contained on the shield board 630.

Isolating the control circuitry in a separate EMI shield chamber may prevent damage to or malfunction of the control circuitry as a result of the high EMI levels generated by the pulse circuitry. Such shielding is especially important when the control circuitry is configured to accumulate monitored data over many discharge pulses and is configured to store the accumulated data to non-volatile memory upon power-down. Operational failure under such conditions, often manifested as an unexpected system restart, may result in the system's inability to properly store the accumulated data and the loss of some or all of the accumulated data. While some embodiments of a pulse generator may address the risk posed by the high EMI levels through increased separation of the pulse generator circuitry and the control circuitry, other embodiments may locate all electronic circuitry in as small a physical volume as possible. The housing 602 with EMI shielded chambers thus enables the pulse generator to be relatively small and portable. Shielding of the data interface is beneficial for enhancing electro-magnetic compatibility between the pulse generator and external systems to which the pulse generator may be connected. The utility of such shielding is further enhanced by the continuous use of the data interface during active operation of the pulse generator for reporting pulse-by-pulse data back to the external host.

One or more of the chambers 601, 611, 621 may also be potted with a potting material 609 such as an epoxy. Potting may prevent internal breakdown (e.g., due to corona effects) of the circuit components. In one embodiment, the shield board 630 may include holes that allow the potting to flow from one or both of the chambers 601, 611 down into the chamber 621. The potting also allows the form factor of the generator to be smaller because the dielectric breakdown voltage of the potting is much higher than air. The potting also makes the electronics more resistant to environmental factors such as moisture, dust and vibration and aids in the efficient removal of waste heat from the electronics.

According to one potting process, the potting material may be applied in air and then cured under vacuum. According to another potting process, the potting material may be applied under vacuum. Both processes minimize the formation of bubbles in the potting mixture, which may cause internal breakdown and damage if the bubbles form near the high voltage circuit nodes.

Accordingly, embodiments described herein provide pulse generators and spectroscopy systems with various advantages. Consistent with one embodiment, a spectroscopy system includes: discharge pulse circuitry configured charge and discharge for generating electrical discharge pulses; monitor circuitry configured to measure characteristics of pulse generator operation including characteristics quantifying the discharge pulses generated by the discharge pulse circuitry; control circuitry configured to control charging and generation of the discharge pulses and to collect measurements from the monitor circuitry to produce pulse generator data representative of measured characteristics, the pulse generator data including discharge pulse data quantifying accumulated discharge pulses generated by the discharge pulse circuitry; electrodes coupled to the discharge pulse circuitry; and a spectroscopy detector configured to measure and analyze spectroscopic emissions resulting from the electrical discharge pulses generated between the electrodes.

Consistent with another embodiment, a spectroscopy system includes: discharge pulse circuitry configured to charge and discharge for generating electrical discharge pulses; monitor circuitry configured to measure characteristics of pulse generator operation including characteristics quantifying the discharge pulses generated by the discharge pulse circuitry; control circuitry configured to control charging and generation of the discharge pulses, to collect measurements from the monitor circuitry to produce pulse generator data representative of measured characteristics, and to report pulse generator data corresponding to individual discharge pulses to a user on a pulse-by-pulse basis following initiation of the individual discharge pulses; electrodes coupled to the discharge pulse circuitry; and a spectroscopy detector configured to measure and analyze spectroscopic emissions resulting from the electrical discharge pulses generated between the electrodes.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A spectroscopy system comprising:
   discharge pulse circuitry configured to charge and discharge for generating electrical discharge pulses;
   monitor circuitry configured to measure characteristics of pulse generator operation including characteristics quantifying the discharge pulses generated by the discharge pulse circuitry;

control circuitry configured to control charging and generation of the discharge pulses, to collect measurements from the monitor circuitry to produce pulse generator data representative of measured characteristics, and to report pulse generator data corresponding to individual discharge pulses on a pulse-by-pulse basis following initiation of the individual discharge pulses wherein the control circuitry is configured to adjust an operating parameter in response to the pulse generator data by increasing a pulse initiation control parameter in response to a calculated decrease in the probability of discharge pulse as represented by the pulse generator data;

electrodes coupled to the discharge pulse circuitry; and a spectroscopy detector configured to measure and analyze spectroscopic emissions resulting from the electrical discharge pulses generated between the electrodes.

2. The spectroscopy system of claim 1 further comprising data processing circuitry configured to receive pulse generator data and to correlate spectroscopic emissions data with the pulse generator data that produced the emissions.

3. The spectroscopy system of claim 1 wherein the pulse generator data reported by the control circuitry includes data selected from the group consisting of a discharge pulse magnitude value, a discharge pulse duration value, a discharge pulse generation delay value relative to a trigger, and a tag value indicative of a non-compliant discharge pulse.

4. The spectroscopy system of claim 1 wherein the control circuitry is configured to report to an external user when values of the pulse generator data fall within or outside a predefined range.

5. The spectroscopy system of claim 1 wherein the control circuitry is configured to halt system operation in response to the pulse generator data.

6. The spectroscopy system of claim 1 wherein the control circuitry includes trigger generation circuitry configured to generate a trigger initiation signal, and wherein the discharge pulse circuitry is configured to generate a high-voltage initiation pulse in response to the trigger initiation signal and wherein the time delay between the trigger initiation signal and the high-voltage initiation pulse is on the same order of magnitude as a duration of the discharge pulse that is generated.

7. The spectroscopy system of claim 1 wherein the discharge pulse circuitry is configured to generate multiple discharge pulses following a single, high-voltage initiation pulse in response to a single trigger initiation signal from the control circuitry.

8. The spectroscopy system of claim 1 further comprising a housing forming at least a first EMI shielded chamber enclosing and isolating the input power and data connections.

9. The spectroscopy system of claim 8 wherein the housing forms at least a second EMI shielded chamber enclosing and isolating the control circuitry and wherein the control circuitry includes a digital processor.

10. The spectroscopy system of claim 1 wherein the discharge pulse circuitry includes a resonant transformer trigger circuit configured to drive a trigger transformer in response to a trigger initiation signal having a waveform to excite an energy storage resonance between the trigger transformer and a set of reactive electronic components coupled to the transformer to generate a high-voltage initiation pulse.

11. The spectroscopy system of claim 1 wherein the discharge pulse circuitry includes a transformer trigger circuit configured to charge and switch a trigger transformer in response to a trigger initiation signal to generate a high-voltage initiation pulse and wherein the high-voltage initiation pulse occurs after the trigger initiation signal is terminated.

12. The spectroscopy system of claim 11 wherein at least a subset of the pulse generator data represents a voltage amplitude of the high-voltage initiation pulse associated with the discharge pulse.

* * * * *